United States Patent [19]

Morganti

[11] Patent Number: 4,863,950
[45] Date of Patent: Sep. 5, 1989

[54] MEDICINAL FORMULATION FOR PROMOTING KERATINOGENESIS AND REDUCING SEBORRHEA OF THE FACE AND SCALP

[76] Inventor: Pier F. Morganti, 49 Via Montoggio, 00168 Roma, Italy

[21] Appl. No.: 867,609

[22] Filed: May 27, 1986

Related U.S. Application Data

[63] Continuation of Ser. No. 710,970, Mar. 12, 1985, abandoned, which is a continuation of Ser. No. 364,942, Apr. 2, 1982, abandoned.

[51] Int. Cl.$^4$ .......................... A61K 7/06; A61K 7/48; A61K 7/50
[52] U.S. Cl. ............................... 514/419; 424/DIG. 1; 424/DIG. 2; 424/DIG. 4; 424/70; 424/72; 514/774
[58] Field of Search ................... 424/70, 72, DIG. 1, 424/DIG. 4, DIG. 2; 514/419, 774

[56] References Cited

U.S. PATENT DOCUMENTS

| | | | |
|---|---|---|---|
| 2,558,065 | 6/1951 | Tice | 514/774 |
| 3,089,823 | 5/1963 | Czarnocki | 574/774 |
| 3,395,236 | 7/1968 | White | 514/21 |
| 3,574,820 | 4/1971 | Johnson et al. | 514/774 |
| 3,653,934 | 4/1972 | Rolle | 574/774 |
| 3,663,687 | 5/1972 | Evans | 574/774 |
| 3,950,542 | 4/1976 | Kalopissis et al. | 424/DIG. 4 |
| 4,035,492 | 7/1977 | Kalopissis et al. | 424/DIG. 4 |
| 4,073,898 | 2/1978 | Bouillon et al. | 424/DIG. 4 |
| 4,139,635 | 2/1979 | Kalopissis et al. | 424/DIG. 4 |
| 4,151,301 | 4/1979 | Kalopissis | 424/DIG. 4 |
| 4,208,402 | 6/1980 | Bore | 574/774 |

FOREIGN PATENT DOCUMENTS 0034915  3/1978  Japan .................................. 514/774

OTHER PUBLICATIONS

Merck Index, 6th Edition, 1952, pp. 303 & 304.
Thompson Food Drug Administration Consumer, 2/1981, pp. 10 & 12.

*Primary Examiner*—Dale R. Ore
*Attorney, Agent, or Firm*—Marshall & Melhorn

[57] ABSTRACT

Spherules of gelatin of the "soft" type containing cystin as activating substance, are used for stimulating and improving the keratinogenesis and reducing the seborrhoea of the face and of the scalp, by effect of a synergic activity of the components.

10 Claims, No Drawings

MEDICINAL FORMULATION FOR PROMOTING KERATINOGENESIS AND REDUCING SEBORRHEA OF THE FACE AND SCALP

This application is a continuation of application Ser. No. 710,970, filed Mar. 12, 1985, now abandoned which is a continuation of application Ser. No. 364,942 Apr. 2, 1982, also now abandoned.

This invention refers to a medicinal preparation having the object of promoting keratinogenesis, that is of reinforcing the formation of hair and nails as well as reducing seborrhoea of the skin of the face and of the scalp.

Gelatin (denominated officially in the official Pharmacopoeia "F. U. Gelatin" or according to the international denomination "Gelatinum") is a known substance which is used, particularly, for the production of medicinal capsules.

The use is also known, especially in the pharmaceutical industry, of capsules made of gelatin so-called "soft" which are used as containers of various pharmaceutical active principles. Such capsules, known in fact as soft gelatin capsules, are produced with a particular process of fusion completely automatic and continuous known as the Scherer method ("rotary die process") as described, for example, in U.S. Pat. Nos. 2,318,718, 2,356,436, 2,333,433, 2,379,816, 2,379,817, 2,451,141, or through other methodologies.

Such process involves melting of the gelatin with glycerin, sorbitol and other substances suitable for improving its physical properties, in order to obtain as final product a unity of "soft" gelatin as is well known in the art. During or after melting, gelatin may be also additioned with other active principles (proteins, amino acids, mineral salts, vitamins, etc.) thermally stable at 70° C.

It is also known that it is possible to produce noticeable modifications in proteins having a high sulphur content, enrichening the diet of sheep with cystein or with sulphured amino acids. To this end see Reis P. J. and Schinckel P. G. (1963) Aust. J. Biol. Sci. 16, 218; Reis P. J. (1965) Aust. J. Biol. Sci. 18, 671; Gillespie J. M. Broad A. and Reis P. J. (1969) Biochem. J. 112,41; Broad A., Gillespie J. M. and Reis P. J. (1970) Aust. J. Biol. Sci. 23,149; Frenkel M., Gillespie J. M. and Reis P. J. (1974) Aust. J. Biol. Sci. 27,31.

Adding also collagen gelatins to the diet it is possible to see a further increase of the keratinic fraction having a high sulphur content (Gillespie J. M., Reis J. P. and Schinckel P. G. (1964)Aust. J. Biol. Sci. 17, 532.

It is equally known how the oral assumption of gelatin increases significantly the degree of hardness of nails solving problems of nail fragility (see for example Thyson T. T. (1950) J. Invest. Dermatol, 14, 323).

The surprising effect which gelatin has been found to have on keratinogenesis seems to be attributable to a "specific dynamic action" carried out by the high percentage of glycin it contains (see Michaelson J. B. and Huntsman D. (1963) J. Soc. Cosmet. Chem. 14, 443.

The observation also seems to have a certain importance, that the protein chains of the gelatin are formed by amino acids present in the same proportions and arranged in a similar way with respect to corresponding amino acids of the keratins, with the only exception of cystine.

In the description and claims according to the invention, the term "cystine" is exclusively intended as the form of levo-cystine, with the exclusion of the optically isomeric form of the dextro-cystine.

On the other hand Bigwood E. J. and Robazza F. (1955) have found in the hair of african children affected by Kwashiorkor, a level of cystine below that of other healthy children which live in the same area (see Bigwood E. J. and Robazza F. (1955) Voeding 87, 251).

It has been later observed that hyponutrition delays the rythm of growth, the diameter and resistance to tension of the hair of pigs the diet of which had been modified in order to obtain marasmatic and Kwashiorkorlike conditions (see Cabak V., Gresham G. A. and McCance R. A. (1962) Brit. J. Nitr. 16, 635).

Finally, in the recent years it has been clearly shown that the relative type and proportions of the proteins forming the corneous keratins take up a decisive role in determining certain mechanical properties. In fact, while the principal factor of stabilization of the keratinic structures of hair and human nails is represented by the disulfide bridges and therefore by the presence of proteins having a high content in cystine, proteins should not be neglected of the matrix rich in glycerin and tyrosin which, although present in human hair in small quantities, seem to contribute in a significant way in the stability and resistance of the keratinic structures of several animals (see Bendit E. G. and Gillespie J. M. (1978) Biopolymers 17, 2743).

The sebonormalizing action is also known as well as the elective stimulating action carried out by the cystine in keratinization processes of the hairy structures, which therefore result all the more resistant the higher their cystine content is. In fact, due to its sebo regulating action and due to its action which controls the keratinization of the skin and nails, cystine is used in the treatment of seborrhoic conditions in general. It is used in the treatment of onicodistrophies and in the nail and hair fragility in doses from 1 to 2 g a day.

It has now been discovered according to the invention that solid spherules of gelatin produced according to the Scherer method and therefore formed by gelatin and glycerin or sorbitol, added with a certain quantity of cystine, orally administered in daily doses comprising about 800 mg of cystin in 2 g of gelatin, have an improving and stimulating effect on keratinogenesis and at the same time, reducing the seborrhoea both of the face and of the scalp.

According to the invention this effect is due to the association of "soft" gelatin with cystine, offering results which are superior to those yielded by presently available formulations which contain only gelatin or only cystine, or which contain both in different proportions.

In fast, today formulations do not exist on the market which are formed by so-called "soft" gelatin which contain also cystine and it will be noticed that the doses indicated by the available literature in order to obtain the desired effects are much higher (3 to 6 g of gelatin per day or 1 to 2 g per day of cystine) with respect to the dose according to the formulation of the present invention which contains only 2 g of soft gelatin and 800 mg of cystine, to be administered a day.

The fact should be particularly pointed out that cystine which forms the activating agent is not contained in the gelatin in the usual way in which the active principles are contained in normal gelatin capsules, but the levo-cystine is distributed in a homogeneous way in a solid spherule, with no cavity, in the indicated proportions.

According to the invention in fact the intimate distribution of the cystine within the mass of "soft" gelatin ensures a particularly favorable oral absorption, so that it is possible to reduce the doses of active substances with respect to the doses established by the prior art for the indicated pharmaceutical use. To the end of demonstrating the synergistic effect of the ingestion of cystine and gelatin through administration of soft gelatin capsules, experiments have been carried out on rats in which the condition of sufference of the air was induced by means of a biotine free diet. It is in fact known how the alimentary insufficiency of biotin induces, in the rat, the formation of a seborrhoic clinical condition, characterized by the increase of the sebaceous secretion and by the fall of the hairs.

In order to have a direct comparison, said rats have been successively treated, in different lots, with diets added respectively with gelatin, cystine, gelatin-cystine in mechanical mixture and gelatin-cystine in soft spherules.

EXPERIMENTAL TEST 1

Methods and materials

60 Whistar rats were employed of both sexes (30 males and 30 females) of the average weight of 150 g±9. Following the Kalopissis et al methodology (U.S. patent No. 3629452) 50 rats were kept on a biotin free diet for about 40 days until the development was obtained of an evident seborrhoic clinical condition, while the remaining 10 served as controls. After obtaining the desired clinical condition with the development of seborrhoea and loss of hair in various zones, the 50 rats were subdivided into five groups of 10 rats each and treated as follows:

1st group: biotin free diet added with cystine;
2nd group: biotin free diet added with gelatin;
3rd group: biotin free diet added with cystine and gelatin in mechanical mixture;
4th group: biotin free diet added with the mixture of gelatin/cystine melted in soft spherules;
5th group: biotin free diet;
6th group: control.

The diets were administered weekly in the cages of the rats in accurately weighed quantity so that the rats, kept in single cages, would ingest together with the feed, respectively:

- 1st group: 84 mg per kg a week of cystine;
2nd group: 203 mg per kg a week of gelatin from collagen;
3rd group: 84 mg per kg a week of cystine and 203 mg per kg a week of gelatin;
4th group: 280 mg per kg a week of the melted mixture of gelatin/cystine composted of 79.8 mg of cystine and 200.2 mg of gelatin.

After three weeks of treatment and after taking about 200 mg of hairs per rat, all the animals, included the controls, are sacrificed in a chloroform saturated environment in order to control their skin total lipids and in order to carry out possible histological and bioptic examinations.

Determination of the sulphur content of the hairs

The hairs of all the animals (about 100 mg), accurately deterged with alcohol and ethyl ether, and dried, are used for the determination of the total sulphur carried out by titration according to he McDonald methodology (McDonald A. M. G. (1959) Industr. Chem. 35, 33). The results expressed as sulphur percentage with respect to the dried weight of the hairs, are given in table 1.

Determination of the total lipids

Immediately after sacrificing the animals, dorsal samples of skin were taken, which, freed from the paniculus adiposus, have been used both for the determination of the total lipids as well as for the histochemical studies.

The content of the total lipids was determined gravimetrically through the difference in weight of the sample before and after the extraction in Soxhlet with acetone for 10 days and further drying out in vacuum on $P_2O_5$ and paraffin for 24 hours. The values, expressed in percentage, are listed in table 1.

TABLE 1

| | | | Effects on the skin and hairs of the rats kept on a biotin poor diet. | | | | |
|---|---|---|---|---|---|---|---|
| Group | Number of specimens | Biotin poor diet | Additive | Total lipides % | Number of determinations | Sulphur content (× g hair, %) | Number of determinations |
| I | 10 | Yes | Levo-cystine | 38.1 ± 2.987° | 30 | 2.48 ± 0.066° | 20 |
| II | 10 | Yes | Gelatin | 43.5 ± 3.005° | 30 | 2.44 ± 0.08° | 20 |
| III | 10 | Yes | Levo-cystine∞ and gelatin | 35.8 ± 2.796° | 30 | 2.74 ± 0.062° | 20 |
| IV | 10 | Yes | Levo-cystine and gelatin | 26.9 ± 3.111° | 30 | 3.19 ± 0.075° | 20 |
| V | 10 | Yes | — | 46.2 ± 3.102° | 30 | 2.32 ± 0.067 | 20 |
| VI | 10 | No | — | 29.7 ± 3.015 | 30 | 3.90 ± 0.081 | 20 |

°= $P < 0.05$ versus group VI (controls).
∞= mechanical mixture.
= mixture obtained by melting according to the Scherer process.

Comments and results

As it can be seen from table 1, in the rats kept on a biotin poor diet it is possible to notice a reduction of the sulphur in the hairs of about 15% and a global increase of the total lipids of the skin of about 50%. If furthermore the data are observed relating to the individual treatments, it may be clearly seen how the oral assumption of the cystine alone (12 mg/kg/die) causes, in the biotin-poor rats, an increase of the total sulphur of the hair of about 7% ($P<0.05$) and a reduction of the total lipids of the skin of about 15% ($P<0.05$). The oral assumption of gelatin alone, on the contrary, while raising the sulphur content of the hairs of about 5% ($P<0.05$) does not cause any reduction of the lipidic condition of the skin of the biotin-poor rats.

Furthermore the combined action of the cystine and gelatin, which, added in the diet, demonstrates to possess a synergic action of stimulation both with regard to the keratinogenesis as well as to the lipogenesis, appears also very interesting. In fact both the increase found at the level of the total sulphur in the hair and the reduction of the lipids in the skin in rats fed on a biotin poor diet with levo-cystine and gelatin, appears to be greater than the summation of the action obtained singularly both with the levo-cystine and the gelatin. Such action synergism increases noticeably if the simple mechanical mixture is substituted with the same mixture obtained by melting through the Scherer process. In fact, at equal concentration both of cystine and of gelatin, almost a doubling is observed of the action demonstrated both at the keratinogenesis and lipogenesis level.

EXPERIMENTAL TEST 2

The elective stimulting action has also been verified on rats, performed especially by the gelatin-cystine, in the keratinization processes of the hairy structures, verifying the average content of sulphur and cystine of the hairs of rats kept on a normal diet and respectively of rats kept on a biotin poor diet, fed respectively only with gelatin, only with cystine and with the association of gelatin-cystine both in the form of mechanical mixture in hard capsules, and in the form melted in soft spherules.

Materials and methods

110 Whistar rats of both sexes were employed (55 males plus 55 females) of the average weight of 150 g±9, divided in two lots of respectively 60 (lot I) and 50 (lot II) rats each. Following the Kalopissis and Manoussos methodology already quoted in test 1, 50 rats of lot I were kept on a biotin poor diet for about 40 days until the appearance was induced of an evident seborrhoic clinical condition, while the remaining 10 served as controls. After having obtained the desired clinical condition with the appearance of seborrhoea and loss of hairs in several zones, the 60 rats were divided into six groups of 10 rats each and treated as follows:
1st group: normal laboratory diet (controls);
2nd group: biotin free diet;
3rd group: biotin free diet added with cystine;
4th group: biotin free diet added with gelatin;
5th group: biotin free diet added with cystine and gelatin in mechanical mixture (hard capsules);
6th group: biotin free diet added with melted mixture of gelatin-cystine (soft spherules).

The diets prepared specifically by a specialized firm were administered weekly in the cages of the rats, in accurately weighed quantity so that the rats, kept in single cages, would ingest together with the feed, respectively:
1st group: normal diet;
2nd group: biotin (BC) poor diet;
3rd group: diet BC+84 mg per kg weekly of cystine;
4th group: diet BC+203 mg per kg weekly of gelatin FU;
5th group: diet BC+84 mg per kg weekly of cystine and 203 mg per kg weekly of gelatin FU (hard capsules);
6th group: diet BC+280 mg per kg weekly of the melted mixture of gelatin-cystine composed of 79.8 mg of cystine and of 200.2 mg of gelatin (soft spherules).

After six weeks of treatment and after having taken about 1 g of hairs per rat, all the animals included the controls are sacrificed in a chloroform saturated ambient.

The 50 rats of the second lot (normal rats, not subjected previously to a biotin poor diet), divided into five groups of 10 rats each, have been fed respectively with:
1st group: normal laboratory diet (DN) (controls);
2nd group: DN+cystine;
3rd group: DN+gelatin FU
4th group: DN+gelatin and cystine in mechanical mixture (hard capsules);
5th group: DN+gelatin and cystine previously melted together (soft spherules).

The quantity of the feed placed in the cages was calculated in such a way that the rats would ingest the same quantity per kg of cystine, FU gelatin or gelatin-cystin already described above.

After 150 days of treatment the rats, under ether anaesthesia, were partially depilated with a razor.

Determination of the sulphur content of the hairs

A part of the hairs (about 100 mg) of all the animals of the two groups, accurately deterged with alcohol and ethyl ether and dried, are used for the determination of the total sulphur carried out by means of titration, according to the previously mentioned McDonald methodology. The results expressed as percentage of sulphur with respect to the dried weight of the hairs, are listed in tables 2 and 3.

Determination of the cystine content in the hairs

After having hydrolized the hairs of all the animals (about 800 mg) previously deterged as already described, the quantity was determined of cystine using the autoanalyzer.

The results expressed as g/100 g of hairs are listed in tables 2 and 3.

Determination and isolation of the proteins in the hair

The extraction of the total cheratins of the hairs was carried out with the method of the urea-thioglycolate according to the method described in Gillespie J. M., Reis P. J. and Schinckel P. G. (1964) Aust. J. Biol. Sci. 17, 548.

After determining from one portion the total keratin (total proteins), the keratin fraction at high sulphur content is separated through alkylation with iodo acetate, dialysis and precipitation of the protein at low sulphur content with zinc acetate at pH 6. The total sulphur was determined on the protein fraction "rich in sulphur" according to the already mentioned McDonald methodology. The results are listed in tables 2 and 3.

TABLE 2

Variation of the proteic content of the cheratins of biotin poor rats fed on a gelatin-cystine enriched diet.

| Treatment | Sulphur content % | Cystine content % | Total proteins % | "Sulphur rich" proteic fraction % | Sulphur contained in the "sulphur rich" proteic fraction, % |
|---|---|---|---|---|---|
| Normal diet (control) | 3.90 ± 0.081° | 12.0 ± 1 | 90 ± 1 | 24 ± 2 | 5.9 ± 0.2 |
| Biotin poor diet (BC) | 2.32 ± 0.07° | 8.0 ± 0.5 | 91 ± 2 | 17 ± 1 | 3.3 ± 0.03 |

TABLE 2-continued

Variation of the proteic content of the cheratins of biotin poor rats fed on a gelatin-cystine enriched diet.

| Treatment | Sulphur content % | Cystine content % | Total proteins % | "Sulphur rich" proteic fraction % | Sulphur contained in the "sulphur rich" proteic fraction, % |
|---|---|---|---|---|---|
| BC/levo-cystine | 2.48 ± 0.07$^o$ | 9.3 ± 0.6 | 90 ± 1 | 20 ± 1 | 3.9 ± 0.05 |
| BC/gelatin | 2.44 ± 0.08$^o$ | 9.1 ± 0.8 | 90 ± 1 | 18 ± 0.5 | 3.6 ± 0.04 |
| BC/levo-cystine/gelatin | 2.74 ± 0.06$^o$ | 10.3 ± 0.5 | 91 ± 2 | 27 ± 1 | 4.3 ± 0.05 |
| BC/levo-cystine gelatin | 3.19 ± 0.07$^o$ | 12.0 ± 0.8 | 90 ± 1 | 28 ± 1 | 4.9 ± 0.08 |

$^o$P = 0.05 versus normal diet.

TABLE 3

Variations in the composition of keratin of the hairs of rats fed on a gelatin-cystine enriched diet.

| Treatment | Sulphur content % | Cystine content % | "Sulphur rich" keratin % | Sulphur contained in the "sulphur rich keratin" % |
|---|---|---|---|---|
| Normal diet (DN) | 3.3 ± 0.1$^o$ | 11.8 ± 0.5$^o$ | 21.0 ± 0.5$^o$ | 4.7 ± 0.1$^o$ |
| DN/levo-cystine (84 mg/kg weekly) | 3.6 ± 0.1$^o$ | 13.8 ± 0.6$^o$ | 25.9 ± 0.5$^o$ | 5.1 ± 0.2$^o$ |
| DN/gelatin (203 mg/kg weekly) | 3.1 ± 0.1$^o$ | 11.5 ± 0.5$^o$ | 23.9 ± 0.6$^o$ | 4.5 ± 0.1$^o$ |
| DN/gelatin/cystine (203 + 84 mg/kg weekly), hard capsules | 3.8 ± 0.2$^o$ | 14.3 ± 0.5$^o$ | 31.7$^o$ + 0.5$^o$ | 5.5 ± 0.2$^o$ |
| DN/gelatin/cystine (280 mg/kg weekly), soft spherules | 4.2 ± 0.2$^o$ | 15.5 ± 0.6$^o$ | 32.5 ± 0.6$^o$ | 6.1 ± 0.2$^o$ |

$^o$P = 0.05 versus normal diet.

Comments and results

From table 2 it can be seen how between the group of rats on the biotin poor diet and the control group significant differences can be seen (P<0.05) at all levels. In fact, the lack of biotin causes in the rat a reduction of the total sulphur present in the hair of about 50%. Such reduction, considering the analytical difficulties, seems to be totally due to a corresponding decrease in the content of cystine (about 40% P<0.05).

It is interesting to notice furthermore how the reduction both of the sulphur and of the cystine is accompanied by a noticeable reduction (about 50%) of the protein fraction so-called "rich at sulphur" present essentially, as known, in the matrix of the hair. As the rats are gradually fed with the diet enriched with cystine and the mixture of gelatin-cystin, a significant protein increase noticeable at the level of the protein fraction of the matrix of the hair is noticed. The protein increase is accompanied always by a corresponding increment in cystine.

Observing the data concerning the rats lacking biotin fed respectively with gelatin, cystine and cystin-gelatin both in the form of hard capsules and of soft spherules it is proven that the alimentary enrichment with gelatin alone, in the dosages employed, while it does not seem to be able of bringing significant improvements in the global mass of parameters taken into consideration, if administered together with cystine, it boosts its activity in a substantial way.

In fact, while the addition in the diet of cystine alone increases the parameters taken into consideration, the alimentary enrichment with gelatin-cystine seems to be able practically to bring back to normal the values related to the matrix keratins (fraction "rich at sulphur) and of the cystine of the hair itself. The gelatin-cystine administered in the pharmaceutical form of soft spherules (premelting of the gelatin-cystine) seems to be able also to further increase the incorporation of the cystine at the level of the matrix of the hair, may be due to the different bioavailability proven by such pharmaceutical form.

From the data concerning normal rats fed for a long period (20 weeks) with diets enriched with gelatincystine and mixture of the two (table 3) a progressive increase is immediately seen of the sulphur, of the cystine and of the keratin fraction "rich in sulphur" of the matrix of the hair. An increment is obtained in fact of the keratin fraction "rich in sulphur" which ranges from 10% for the rats fed with only gelatin to 50% for the rats fed with the association of gelatin and cystine administered in the form of soft spherules. It seems therefore clear that the increase of the cystine which can be found in the hair of rats fed with a diet enriched with gelatin-cystine is due especially to the increase of the proteins of the matrix of the hair. The gelatin, probably due to its high content in glycin, seems to be capable of increasing noticeably the incorporation of the cystine in the keratin fraction (rich in sulphur) of the matrix of the hair. Such increase appears to be greater, furthermore depending on the pharmaceutical form used probably due to a different bioavailability of the feed itself. In fact, as it can be seen from table 2, the major content of cystine has been found in the hair of rats fed with the enriched diet with the association of gelatin and cystine in the form of soft spherules (premelted mixture). Such diet has caused also the major increment both of the protein fraction "rich in sulphur" (+50%) as well of the cystine which can be found in the hair (+33%) of the rats treated with respect to the controls (P<0.05).

EXPERIMENTAL TEST 3

Experimental test on humans

To the end of verifying the possible stimulating selective action performed by glycin and gelatin in the keratinizing processes of the hairy structures, a study has been conducted in order to control the possible beneficial effect deriving from enrichment of the human diet with gelatin and cystine in well defined proportions.

B product, to about 100 mg of gelatin and 300 mg of starch.

The results are listed in table 4.

TABLE 4
Effects on the hair of gelatin-cystine after a three months treatment.

| Treatment | Medium fibers per cm² | Medium sites per cm² | Medium fibers per sites | Increase % | Medium diameter μm | Increase % | Sulphur content (× g hair) % | Increase % | Medium content free thiols μm × g hair | Reduction % |
|---|---|---|---|---|---|---|---|---|---|---|
| Gelatin/cystine | before 155.3 ± 48° | 84.2 ± 15 | 1.84 ± 0.49 | 49.4° | 61.5 ± 5.4 | 35° | 3.82 ± 0.08 | 26.7° | 251 ± 30 | 62.9° |
| | after 270.6 ± 37° | 98.5 ± 17 | 2.75 ± 0.21 | | 83.2 ± 8.1 | | 4.84 ± 0.10 | | 93 ± 15 | |
| Placebo | before 167.5 ± 33 | 79.3 ± 16 | 2.11 ± 0.63 | — | 67.3 ± 8 | — | 3.91 ± 0.11 | — | 192 ± 25 | — |
| | after 174.0 ± 39 | 82.9 ± 20 | 2.09 ± 0.37 | | 61.0 ± 10 | | 3.74 ± 0.12 | | 173 ± 19 | |

° = P 0.05
°° = P 0.005
— = insignificant tions.

Materials and methods 40 voluntary Italian people have been selected having dark hair, suffering from a Effluvium capillitii, of both sexes and of ages between 20 and 40. All voluntary patients received, through the double blind technique, a bottle containing spherules of gelatin-cystine (product A) of spherules of placebo (product B). Before beginning the experimentation and after 24 hours from the last time the hair had been washed, the number was checked with an illuminated magnifying glass of the follicular orifices (sites) and the number of hairs (fibers) emerging from each site, carrying out the count in a well defined area (1 cm × 1 cm) between the rear vertex (VP) and the front vertex (VA), according to the Moretti subdivision (Moretti G., Baccaredda-Boy A. and Rebora A. (1969) in "W. Montagna and R.L. Dobson" "Advances in Biology of the Skin", Vol. IX, "Hair Grow", Pergamon Press, Oxford, page 538).

Methodology of the count

The count of the sites and fibers has been carried out using a small transparent perspex ruler of 10 cm in length with a center opening of the width of 1 cm², according to the Cottington et al (J. Soc. Cosmet. Chem. 28, 219) methodology, during a period of 3 months. Furthermore, before beginning the treatment, about 200 mg of hair in the area near the counting point had been sampled from all voluntary patients, cutting the sample just barely above the scalp with a well sharpened scissors. During the treatment period the voluntary patients have always used the same shampoo also avoiding the cutting of the hair.

Determination of sulphur and free thiols

After having calculated the means thickness according to the Cottington methodology already mentioned, about 100 mg of the sample hair, previously cleansed with alcohol and ethyl ether, are used to determine the quantity of total sulphur according to the already mentioned McDonald methodology. On the remaining integral portion (about 100 mg) the total number of free thiols is determined amperometrically.

During the three months of treatment, the voluntary patients took during normal meals four spherules a day of the alimentary supplement, equal, for the A product, to 2 g of gelatin and 800 mg of cystine a day, and for the Results and comments As it can be seen from table 4, the average increase of fibers/sites is equal to about 50% with P<0.05. This means that the average of the hairs emerging from the follicular orifices themselves (sites) are doubled within 3 months in those individuals subjected to a diet enriched with gelatin-cystine. As a matter of fact those patients fed with placebo (product B) have undergone no improvement.

Similar results have emerged also with regard both to the total sulphur content, which increases by about 27% (P<0.05), and of the free thiols present on the integral hair, for which a decrease is seen of over 60% (P<0.005). The experimental test demonstrates that the preparation according to the invention may be employed in the human therapy for the cure of seborrhoea.

According to the invention it was found that very satisfactory results are obtained with spherules produced through the Scherer method having the following composition of percentage by weight:

| gelatin | 50–60% |
| glycerin or sorbitol | 18–23% |
| cystine | 20–25% |

The following composition is particularly preferred:

| gelatin | 57% |
| glycerin | 20% |
| cystine | 23% |

The "soft" gelatin per se has the following composition in pecentage by weight:

| gelatin | 55–80% |
| glycerin or sorbitol | 23–30% |

The preferred composition being:

| gelatin | 73.5% |
| glycerin | 26.5% |

It should be particularly noted that the cystine which constitutes the activating agent is not contained in the gelatin in the usual way in which the active principles are contained in normal capsules of gelatin, but the cystine is distributed in a homogeneous way in a solid spherule, having no cavity, in the indicated proportions.

According to the invention, in fact the intimate distribution of the cystine in the mass of "soft" gelatin ensures a particularly favorable oral absorption.

Preferably each spherule will have a total weight of about 900 mg, in which the active substances are subdivided in the following way:

| | |
|---|---|
| gelatin | 450 to 550 mg |
| glycerin or sorbitol | 160 to 200 mg |
| cystine | 180 to 220 mg |

In a partiuclarly preferred embodiment, each spherule contains:

| | |
|---|---|
| gelatin | 500 mg |
| glycerin or sorbitol | 180 mg |
| cystine | 200 mg |

The daily oral dose considered is of 4 spherules a day, so that the total daily dosage appears to be about 2 g of gelatin and 800 mg of cystine.

It is further obvious that the spherules of gelatin may contain other pharmaceutically compatible additives, such as edulcorants, dyes, vitamins, mineral elements, natural extracts and the like, as long as they are thermally stable at 70° C.

The gelatin spherules may be produced through melting of the gelatin itself with glycerin, sorbitol or other substances suited to improve the physical properties according to the "Scherer" method or through similar methodologies which yield as a final product homogeneous units of "soft" gelatin of any whatsoever form and color.

I claim:

1. A composition for reducing lipid content in the skin, the composition comprising soft gelatin and about 20 to 28.5 weight percent of the composition of levo-cystine.

2. A composition as defined in claim 1 in which the amount of levo-cystine is about 23 wt. %.

3. A composition as defined in claim 1 in which a daily administration is provided with about 2 grams of soft gelatin and 800 mg. of levo-cystine.

4. A composition as defined in claim 1 in which the amount of levo-cystine is about 20%

5. A composition as defined in claim 1 in which the amount of levo-cystine is about 25%.

6. A composition as defined in claim 1 in which the soft gelatin contains glycerine or sorbitol as a plasticizer.

7. A composition as defined in claim 1 in which the soft gelatin contains glycerine as a plasticizer.

8. A composition for reducing lipid content of the skin, the composition containing soft gelatin and levo-cystine uni-formly distributed in the soft gelatin, the composition having the following approximate wt.% of ingredients:

| Ingredients | Wt. % |
|---|---|
| gelatin | 50–60 |
| glycerine or sorbitol | 18–23 |
| levo-cystine | 20–25 |

9. A composition as defined in claim 8 in which there is about 57 wt % gelatin, 20 wt % glycerine and about 23 wt % levo-cystine.

10. A composition for reducing the lipid content of the skin by oral administration, the composition comprising a solid, homogenous spherule of about 65 to 80 wt % soft gelatin and distributed uniformly in the soft gelatin, about 20 to 28.5 wt % of levocystine, the daily administration being about 2800 mg of the composition.

* * * * *